(12) United States Patent
Toida et al.

(10) Patent No.: US 6,374,128 B1
(45) Date of Patent: Apr. 16, 2002

(54) BLOOD VESSEL IMAGING SYSTEM

(75) Inventors: Masahiro Toida; Kazuo Hakamata, both of Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/444,378

(22) Filed: Nov. 22, 1999

(30) Foreign Application Priority Data

Nov. 20, 1998  (JP) ............................................ 10-330764
Nov. 20, 1998  (JP) ............................................ 10-330765

(51) Int. Cl.$^7$ ................................................. A61B 5/00
(52) U.S. Cl. ...................... 600/310; 600/476; 600/500; 600/502; 600/504; 600/505; 356/319; 356/450; 356/484; 356/485
(58) Field of Search ................................. 600/407, 322, 600/317, 476, 477, 501, 500, 502, 504, 506; 356/319, 320, 450, 345, 349, 451, 484, 485; 250/200, 227.2, 227.26, 574

(56) References Cited

U.S. PATENT DOCUMENTS

| | | | |
|---|---|---|---|
| 4,109,647 A | | 8/1978 | Stern et al. ................. 128/2.05 |
| 4,834,111 A | * | 5/1989 | Khanna et al. |
| 5,022,157 A | | 6/1991 | Modell ........................ 356/318 |
| 5,106,184 A | * | 4/1992 | Milbocker |
| 5,459,570 A | * | 10/1995 | Swanson et al. |
| 5,807,264 A | | 9/1998 | Palteli ........................ 600/477 |
| 6,037,579 A | * | 3/2000 | Chan et al. |

FOREIGN PATENT DOCUMENTS

GB   2 132 483 A   7/1984 ............ A61B/5/02

OTHER PUBLICATIONS

Japanese ME Academy Magazine BME, vol. 8, No. 5, 1994, pp. 41–50.

* cited by examiner

Primary Examiner—Marvin M. Lateef
Assistant Examiner—Jeoyuh Lin
(74) Attorney, Agent, or Firm—Sughrue Mion, PLLC

(57) ABSTRACT

A blood vessel imaging system includes a measuring light source which emits a measuring light beam. An optical heterodyne detection system consists of an optical system which splits the measuring light beam into a first light beam traveling to impinge upon an organism and a second light beam traveling not to impinge upon the organism and combines the second light beam with the first beam emanating from the organism into a combined light beam, a frequency shifter which causes the first and second light beams to have frequencies different from each other, and a beat component detector which detects beat components of the combined light beam. A band-pass filter detects, out of the beat component detection signal output from the beat component detector, off-centered components in a frequency band deviated from the center frequency of the beat component detection signal by a predetermined width. An image signal is generated according to whether the off-centered beat signal detected by the band-pass filter is higher or lower than a predetermined threshold level.

26 Claims, 11 Drawing Sheets

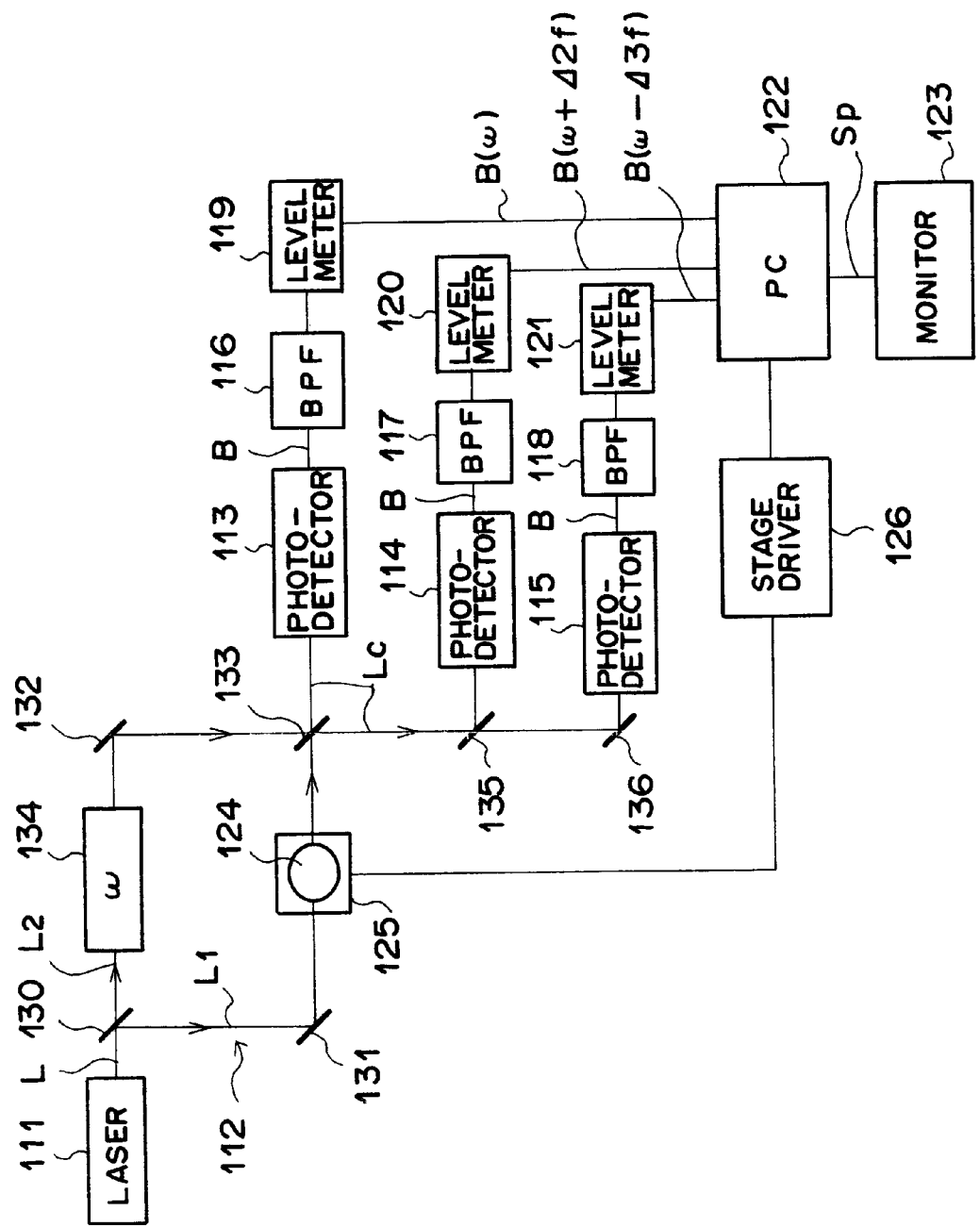
F I G. 7

BLOOD VESSEL IMAGING SYSTEM

BACKGROUND OF THE INVENTION

1. Field of the Invention

This invention relates to a blood vessel imaging system for imaging blood vessels, and more particularly to a blood vessel imaging system which can image blood vessels with arteries and veins distinguished from each other.

This invention further relates to a system which can clearly distinguish arteries and veins from each other.

This invention further relates to a system for measuring the flow rate of light scattering fluid such as arterial blood and venous blood.

2. Description of the Related Art

In the clinical field, there has been a wide demand for imaging arteries and veins clearly distinguished from each other. For example, since arteriosclerosis generally starts at the periphery of the arteries, it will be useful in diagnosing arteriosclerosis if the inner walls of the peripheral arteries can be imaged distinguished from those of the veins.

There has been wide known angiography as a system for imaging blood vessels. However angiography is disadvantageous in that load on the testee is heavy and the testee generally must stay in the hospital.

Further there has been proposed technique for imaging part of an organism on the basis of penetration of light through the part as disclosed in "Japanese ME Academy Magazine BME", vol.8, No.5, 1994, pp.41~50. However it is very difficult to image arteries and veins clearly distinguished from each other by the technique.

SUMMARY OF THE INVENTION

In view of the foregoing observations and description, the primary object of the present invention is to provide a blood vessel imaging system which can image blood vessels with arteries and veins clearly distinguished from each other without exposing the testee to heavy load.

Another object of the present invention is to provide a blood vessel distinguishing system which cyan clearly distinguish arteries and veins from each other without 9 sing the testee to heavy load.

Still another object of the present invention is to provide a flow rate measuring system for measuring the flow rate of light scattering fluid such as arterial blood and venous blood.

In the blood vessel imaging system in accordance with the present invention, an optical heterodyne detection system is employed in order to ensure high spatial resolution to an organism as a scattering medium, and arteries and veins are distinguished from each other on the basis of the fact that the spectral broadening (Doppler broadening) of beat component detection signal output from the heterodyne detection system changes with the flow rate of blood in the blood vessel.

That is, in accordance with a first aspect of the present invention, there is provided a blood vessel imaging system comprising a measuring light source which emits a measuring light beam, a scanning means which causes the measuring light beam to scan an organism, an optical heterodyne detection system consisting,;of an optical system which splits the measuring light beam upstream of the organism into a first light beam traveling to impinge upon the organism and a second light beam traveling not to impinge upon the organism and combines the second light beam with the first beam emanating from the organism into a combined light beam, a frequency shifter which causes the first and second light beams to have frequencies different from each 0 and a beat component detecting means which detects beat components of the combined light beam, a filtering means which detects, out of the beat component detection signal output from the beat component detecting means, off-centered components in a frequency band deviated from the center frequency of the beat component detection signal by a predetermined width, and an image signal generating means which generates an image signal according to whether the off-centered beat signal detected by the filtering means is higher or lower than a predetermined threshold level.

For example, the image signal generating means generates an image signal representing artery parts of the organism on the basis of components of the off-centered beat signal which are higher than the predetermined threshold level, and generates an image signal representing vein parts of the organism on the basis of components of the off-centered beat signal which are lower than the predetermined threshold level.

It is preferred that the blood vessel imaging system be provided with an in-phase time detecting means which detects in-phase times at which broadening of the spectrum of the beat component detection signal becomes of a predetermined phase, and a synchronization detecting means which samples the off-centered beat signal at the in-phase times and inputs the off-centered beat signal thus obtained into the image signal generating means.

The in-phase time detecting means may be, for instance, a means for detecting the pulse wave of the organism, or for detecting the times at which the center frequency component of the beat component detection signal takes a predetermined peak value.

Further it is preferred that the measuring light source comprises a linear or two-dimensional array of a plurality of light emitting portions and the optical heterodyne detection system is arranged to be able to detect in parallel beat components of the combined light beams based on the measuring light beams from the respective light emitting portions, and the measuring light source and the optical heterodyne detection system also function as at least a part of said scanning means.

The beat component detection signal (beat signal) output from the heterodyne detection system described above represents intensity of only straight light components traveling straight through the organism or scattered light components close to the straight light components except influence of scattering by the organism which is a scattering medium.

When a fluid which causes multiple scattering of the measuring light flows in a direction perpendicular to the direction of travel of the measuring light, the peak value of the beat signal is lowered and the spectrum of the beat signal is broadened. For example, FIG. 4A shows a spectrum of the beat signal when the flow rate of the fluid is 0, and FIGS. 4B to 4D show those for different flow rates of the fluid which increase in this order. As can be seen from FIGS. 4A to 4D, the peak value of the intensity of the beat signal becomes lower and the spectrum of the beat signal is broadened (Doppler broadening) as the flow rate of the fluid increases.

Since blood is also a fluid which causes multiple scattering of light, the same phenomenon occurs when the measuring light beam passes through a blood vessel. Since arterial blood is generally higher than venous blood in flow rate, the reduction in the peak value of the intensity of beat signal and broadening of the spectrum are larger when the measuring light beam travels through an artery than when the measuring light beam travels through a vein.

In FIG. 5, line a shows a spectrum of the beat signal when the measuring light beam travels through an artery and line b shows a spectrum of the beat signal when the measuring light beam travels through a vein. When components of the beat signal in a frequency band deviated from the center frequency $\omega$ of the beat signal by a predetermined width $\Delta f$ are detected by use of a band-pass filter having transmission characteristics shown by line c, and an image signal is generated on the basis of components of the off-centered beat signal (made up of components of the beat signal in said frequency band) which are higher or lower than a predetermined threshold level, an image signal representing only artery parts or vein parts of the organism can be generated.

That is, when the predetermined threshold value is set, for instance, at d in FIG. 5, and an image signal is generated on the basis of components of the off-centered beat signal which are higher than the predetermined threshold level d, a signal representing only artery parts of the organism can be generated. On the other hand, when an image signal is generated on the basis of components of the off-centered beat signal which are lower than the predetermined threshold level d, an image signal representing only vein parts of the organism can be generated.

More strictly, broadening of the spectrum of the beat signal due to flow of arterial blood changes with the flow rate of arterial blood. That is, the spectrum of the beat signal at a maximum flow rate of the arterial blood is as shown by line a-1 in FIG. 6 whereas the spectrum of the beat signal at a minimum flow rate of the arterial blood is as shown by line a-2. Broadening of the spectrum of the beat signal is very similar to that of beat signal when the measuring light beam travels through a vein (shown by line b) in a frequency band corresponding to the transmission frequency band of the band-pass filter, and accordingly it is difficult to distinguish the former from the latter.

Accordingly, when in-phase times at which broadening of the spectrum of the beat component detection signal becomes of a predetermined phase (optimally times at which the flow rate of the arterial blood is maximized) are detected, off-centered beat signal is sampled at the in-phase times and the off-centered beat signal thus obtained is input into the image signal generating means, arteries and veins can be imaged clearly distinguished from each other.

Further when a measuring light source comprising a linear or two-dimensional array of a plurality of light emitting portions and an optical heterodyne detection system which can detect in parallel beat components of the combined light beams based on the measuring light beams from the respective light emitting portions are employed so that the measuring light source and the optical heterodyne detection system also function as at least a part of said scanning means, it becomes unnecessary for the scanning means to mechanically cause the measuring light beam to scan the organism in at least one direction, whereby the scanning speed, which results in the imaging speed, can be increased. This is especially advantageous in the case where the off-centered beat signal is sampled at said in-phase times and sampling of the off-centered beat signal requires a relatively long time.

In accordance with a second aspect of the present invention, there is provided a blood vessel imaging system comprising a measuring light source which emits a measuring light beam, a scanning means which causes the measuring light beam to scan an organism, an optical heterodyne detection system consisting of an optical system which splits the measuring light beam upstream of the organism into a first light beam traveling to impinge upon the organism and a second light beam traveling not to impinge upon the organism and combines the second light beam with the first beam emanating from the organism combined light beam, a frequency shifter which causes the first and second light beams to have frequencies different from other, and a beat component detecting means which detects beat components of the combined light beam, a first intensity detecting means which detects the intensity of center frequency components of the beat component detection signal output from the beat component detecting means, a second intensity detecting means which detects the intensity of off-centered components of the beat component detection signal in a frequency band deviated from the center frequency of the beat component detection signal by a predetermined width, and an image signal generating means which generates an image signal on the basis of the ratio of the intensity of the off-centered components of the beat component detection signal to the intensity of the center frequency components of the beat component detection signal.

Preferably, the second intensity detecting means detects the intensities of first and second off-centered components of the beat component detection signal in different frequency bands, and the image signal generating means generates an image signal representing artery parts of the organism on the basis of the ratio of the intensity of the center frequency components to that of the first off-centered components and generates an image signal representing vein parts of the organism on the basis of the ratio of the intensity of the center frequency components to that of the second off-centered components.

In accordance with a third aspect of the present invention, there is provided a blood vessel imaging system comprising a measuring light source which emits a measuring light beam, a scanning means which causes the measuring light beam to scan an organism, an optical heterodyne detection system consisting of an optical system which splits the measuring light beam upstream of the organism into a first light beam traveling to impinge upon the organism and a second light beam traveling not to impinge upon the organism and combines the second light beam with the first beam emanating from the organism into a combined light beam, a frequency shifter which causes the first and second light beams to have frequencies different from each other, and a beat component detecting means which detects beat components of the combined light beam, a spectrum analysis means which obtains the spectrum of the beat component detection signal output from the beat component detecting means, and an image signal generating means which generates an image signal on the basis of a spectral width between two frequencies at which the intensity of the beat component detection signal takes a predetermined value with respect to the intensity of the center frequency components, for instance, a half-width of the spectrum.

As described above, the beat component detect-ion signal (beat signal) output from the heterodyne detection system described above represents intensity of only straight light components traveling straight through the organism or scattered light components close to the straight light components except influence of scattering by the organism which is a scattering medium.

When a fluid which causes multiple scattering of the measuring light flows in a direction perpendicular to the direction of travel of the measuring light, the peak value of the beat signal is lowered and the spectrum of the beat signal is broadened. For example, FIG. 11A shows a spectrum of the beat signal when the flow rate of the fluid is 0, and FIGS. 11B to 11D show those for different flow rates of the fluid which increase in this order. As can be seen from FIGS. 11A to 11D, the peak value of the intensity of the beat signal becomes lower and the spectrum of the beat signal is broadened (Doppler broadening) as the flow rate of the fluid increases.

The ratio $I(\omega+\Delta f)/I(\omega)$, to the intensity $I(\omega)$ of the center frequency components of the beat signal (the components of the beat signal at the center frequency $\omega$), of the intensity $I(\omega+\Delta f)$ of the off-centered components of the beat signal in a frequency band deviated from the center frequency $\omega$ by a predetermined width changes with the flow rate v of the fluid substantially as shown in FIG. 12.

Since blood is also a fluid which causes multiple scattering of light, the same phenomenon occurs when the measuring light beam passes through a blood vessel since arterial blood is generally higher than venous blood in flow rate, the ratio $I(\omega+\Delta f)/I(\omega)$ is larger when the measuring light beam travels through an artery than when the measuring light beam travels through a vein.

Though the intensity I of the beat signal itself fluctuates affected by attenuation due to absorption and/or scattering when the measuring light beam travels through the organism, the intensity ratio, that is, the value obtained by normalizing the intensity $I(\omega+\Delta f)$ of the off-centered components of the beat signal by the intensity $I(\omega)$ of the center frequency components of the beat signal, changes basically depending solely on the flow rate of blood in the manner described above with the influence of the attenuation compensated for.

Accordingly, when the image signal generating means generates an image signal on the basis of the intensity ratio $I(\omega+\Delta f)/I(\omega)$, for instance, so that the image signal takes a higher value as the intensity increases, the artery parts and the vein parts can be imaged to be clearly distinguishable from each other from density and/or brightness.

Since the intensity ratio $I(\omega+\Delta f)/I(\omega)$ corresponds to the spectral waveform of the beat signal, the artery parts and the vein parts can be imaged to be clearly distinguishable from each other also by generating an image signal on the basis of the spectral waveform of the beat signal in place of the intensity ratio $I(\omega+\Delta f)/I(\omega)$ as in the blood vessel imaging system of the third aspect.

That is, in the blood vessel imaging system in accordance with the third aspect of the present invention, the image signal is generated on the basis of a spectral width between two frequencies at which the intensity of the beat component detection signal takes a predetermined value with respect to the intensity of the center frequency components, for instance, a half-width of the spectrum. Since such a spectral width becomes larger as the flow rate of blood increases as can be seen from FIGS. 11A to 11D, the artery parts and the vein parts can be imaged to be clearly distinguishable from each other from density and/or brightness when the image signal is generated, for instance, so that the image signal takes a higher value as the spectral width becomes larger.

Further, since also the spectral width such as the half-width changes basically depending solely on the flow rate of blood in the manner described above with the influence of the attenuation compensated for, the artery parts and parts can be accurately distinguished from each other on basis of the spectral width.

In accordance with a fourth aspect of the present invention, there is provided a blood vessel distinguishing system comprising a measuring light projecting means which projects measuring light onto an organism, and an imaging means which images an artery and/or a vein in the organism on the basis of broadening of a spectrum due to an interaction of the measuring light with the organism.

It is preferred that the imaging means detects frequency components of the measuring light scattered by the organism, detects the half-width of the spectrum of the frequency detection signal and images an artery and/or a vein in the organism on the basis of the half-width.

The imaging means may be a means which detects frequency components of the measuring light scattered by the organism, detects the intensity of off-centered components in a frequency band deviated from the center frequency of the frequency detection signal by a predetermined width and images an artery and/or a vein in the organism on the basis of the intensity.

Further the imaging means may be a means which detects frequency components of the measuring light scattered by the organism, detects the ratio between the intensity of center frequency components of the frequency detection signal and the intensity of off-centered components in a frequency band deviated from the center frequency of the frequency detection signal by a predetermined width and images an artery and vein in the organism on the basis of the intensity ratio.

Further the imaging means may be a means which detects frequency components of the measuring light scattered by the organism on the basis of an optical heterodyne detection signal.

In accordance with a fifth aspect of the present invention, there is provided a blood vessel distinguishing system comprising a measuring light projecting means which projects measuring light onto an organism, and a distinguishing means which distinguishes an artery and a vein in the organism from each other on the basis of broadening of a spectrum due to an interaction of the measuring light with the organism.

It is preferred that the distinguishing means detects frequency components of the measuring light scattered by the organism, detects the half-width of the spectrum of the frequency detection signal and distinguishes an artery end a vein in the organism from each other on the basis of the half-width.

The distinguishing means may be a means which detects frequency components of the measuring light scattered by the organism, detects the intensity of off-centered components in a frequency band deviated from the center frequency of the frequency detection signal by a predetermined width and distinguishes an artery and a vein in the organism from each other on the basis of the intensity.

Further the distinguishing means may be a means which detects frequency components of the measuring-light scattered by the organism, detects the ratio between the intensity of center frequency components of the frequency detection signal and the intensity of off-centered components in a frequency band deviated from the center frequency of the frequency detection signal by a predetermined width and distinguishes an artery and a vein in the organism from each other on the basis of the intensity ratio.

Further the distinguishing means may be a means which detects frequency components of the measuring light scattered by the organism on the basis of an optical heterodyne detection signal.

In accordance with a sixth aspect of the present invention, there is provided a flow rate measuring system for measuring a flow rate of light scattering fluid comprising
  a measuring light projecting means which projects measuring light onto light scattering fluid, and
  an analysis means which analyzes the flow rate of the light scattering fluid on the basis of broadening of a spectrum due to an interaction of the measuring light with the light scattering fluid.

It is preferred that the analysis means analyzes frequency components of the measuring light scattered by the organism, detects the half-width of the spectrum of the frequency detection signal and analyzes the flow rate of the light scattering fluid on the basis of the half-width.

The analysis means may be a means which detects frequency components of the measuring light scattered by the organism, detects the intensity of off-centered components in a frequency band deviated from the center frequency of the frequency detection signal by a predetermined width and analyzes the flow rate of the light scattering fluid on the basis of the intensity.

Further the analysis means may be a means detects frequency components of the measuring light scatter by the organism, detects the ratio between the intensity of center frequency components of the frequency detection signal and the intensity of off-centered components in a frequency band deviated from the center frequency of the frequency detection signal by a predetermined width and analyzes the flow rate of the light scattering fluid on the basis of the intensity ratio.

Further the analysis means may be a means which detects frequency components of the measuring light scattered by the organism on the basis of an optical heterodyne detection signal.

In the blood vessel imaging system in accordance with the fourth aspect of the present invention, an artery and/or a vein is imaged on the basis of broadening of the spectrum due to an interaction of the measuring light with the organism, the artery and/or the vein can be imaged as in the preceding blood vessel imaging systems, where an optical heterodyne detection system is employed.

In all the blood vessel imaging systems of the present invention described above, broadening of the spectrum which corresponds to the flow rate of blood in the blood vessel detected when imaging the artery and/or the vein. Since the arterial blood and the venous blood are different from each other in the flow rate of blood, the artery and the vein can be distinguished from each other on the basis of broadening of the spectrum which corresponds to the flow rate of blood in the blood vessel. Further the flow rate of blood in the blood vessel can be known on the basis of broadening of the spectrum the similar manner, the flow rate of light scattering fluid other than blood can be also known.

BRIEF DESCRIPTION OF THE DRAWINGS

FIG. 7 is a schematic view showing a blood vessel imaging system in accordance with a fourth embodiment of the present invention.

DESCRIPTION OF THE PREFERRED EMBODIMENTS

Figure 1:
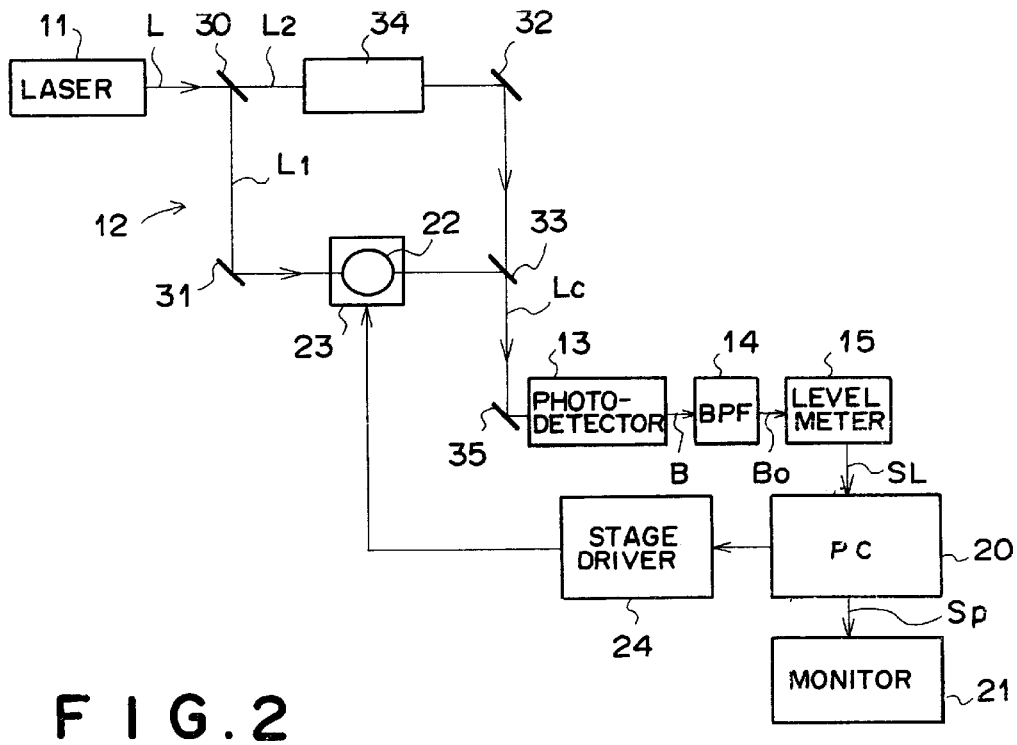
FIG. 1 is a schematic view showing a blood vessel imaging system in accordance with a first embodiment of the present invention.

In FIG. 1, a blood vessel imaging system in accordance with a first embodiment of the present invention comprises a laser 11 emitting a measuring light beam L at a wavelength of λ, an optical heterodyne optical system 12, a photodetector 13 which receives the measuring light beam L emanating from the optical heterodyne optical system 12, a band-pass filter (BPF) 14 which is connected to the photodetector 13 and transmits only a signal in a predetermined frequency band to be described later, and a level meter 15 connected to the band-pass filter 14.

The imaging system further comprises a personal computer (PC) 20 which receives output of the level meter 15 and forms an image signal generating means together with the level meter 15, and an image monitor 21 such as a CRT display connected to the personal computer 20.

Further, there is provided a X-Y stage 23 which is movable in X and Y directions supporting thereon an object (e.g., a human finger) 22. A stage driver 24 drives the X-Y stage 23 under the control of the personal computer 20.

The optical system 12 and the photodetector 13 form an optical heterodyne detection system. The optical system 12 comprises a first half-silvered mirror 30 which splits the measuring light beam L into a first light beam L1 (the part of the measuring light beam L reflected by the first half-silvered mirror 30) and a second light beam L2 (the part of the measuring light beam L passing through the first half-silvered mirror 30), a first mirror 31 which reflects the first light beam L1 to impinge upon the object 22, a second mirror 32 which-reflects the second light beam L2, a second half-silvered mirror 33 which combines the first light beam L1 passing through the object 2 with the second light beam L2 reflected from the second mirror 32 into a combined light beam Lc, and a third mirror 35 which reflects the combined light beam Lc to impinge upon the photodetector 13.

A frequency shifter 34 provided on the optical path of the second light beam L2 shifts the second light b L2 by a predetermined amount so that the center frequency of the second light beam L2 becomes ω. The frequency shifter 34 may comprise for instance, an AOM.

Operation of the blood vessel imaging system of this embodiment will be described, hereinbelow. When taking a blood vessel image, a measuring light beam L is emitted from the laser 11 and the first light beam L1 is projected onto the object 22. While projecting the first light beam L1, the X-Y stage 23 is moved in X and Y directions, whereby the first light beam L1 is caused to two-dimensionally scan the object 22.

When the first light beam L1 passing through the object 22 is combined with the frequency-shifted second light beam L2 by the second half-silvered mirror 33 into a combined light beam Lc, the combined light beam Lc includes therein beat components whose center frequency is ω, equal to that of the frequency-shifted second light beam L2. The output of the photodetector 13 upon receipt of the combined light be Lc includes a beat signal B generated by the beat components. The output of the photodetector 13 is input into the band-pass filter 14.

The beat signal B represents intensity of only straight light components traveling straight through the object 22, which is a scattering medium, or scattered light components close to the straight light components. Accordingly, by obtaining an image signal for the object 22 on the basis of the beat signal B, a high spatial resolution can be ensured though the measuring light beam L (the first light beam L1) is scattered by the object 22.

The band-pass filter 14 selectively transmits signal components in a frequency band near the frequency (ω+Δf) deviated from the center frequency ω of the beat signal B by a predetermined width Δf as shown by line c in Fir 5. The signal passing through the band-pass filter 14, that is, off-centered beat signal Bo, is input into the level meter 15. The level meter 15 measures a level of the off-centered beat signal Bo at a predetermined timing, e.g., at a time at which the off-centered beat signal Bo takes a peak value, and inputs a level signal SL representing the measured level of the off-centered beat signal Bo into the personal computer 20.

Figure 5:
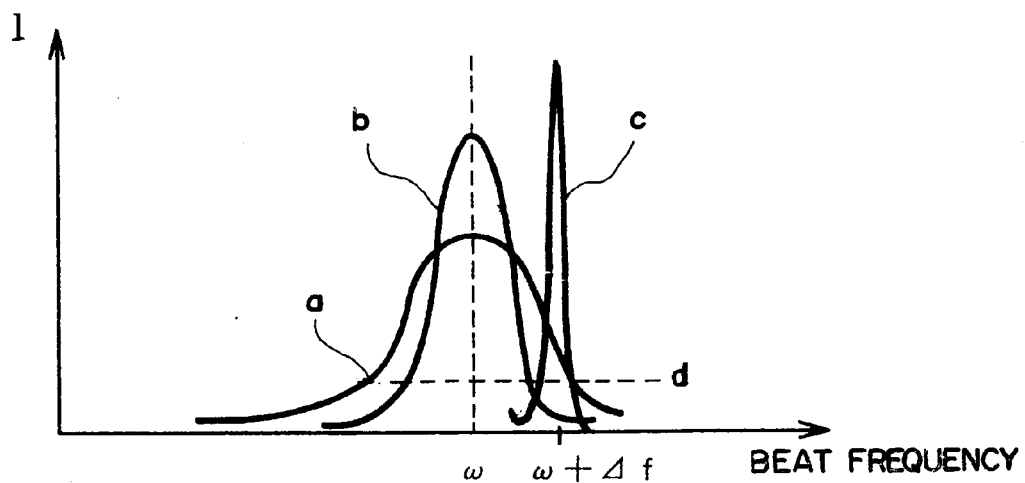
FIG. 5 is a view showing the broadening of the spectrum of the beat signal by flow of blood and the transmission characteristics of the band-pass filter for detecting the off-centered beat signal.

The personal computer 20 compares the level of the off-centered beat signal Bo represented by the level signal SL with a predetermined threshold level such as represented by d in FIG. 5. When an artery is to be imaged, the personal computer 20 generates an image signal component Sp bearing thereon a relatively high density (low brightness) when the level of the off-centered beat signal Bo is higher than the threshold level and otherwise an image signal component Sp bearing thereon a relatively low density (high brightness), and inputs the image signal component Sp into the monitor 21.

The level meter 15 outputs an off-centered beat signal Bo for each scanning spot on the object 22 as the first light beam L1 scans the object 22. Accordingly, the two-valued image signal component Sp is generated for each scanning spot on the object 22.

The image monitor 21 reproduces a two-dimensional image on the basis of an image signal made up of them image signal components Sp thus generated for the respective scan spots. In the image, the artery part is shown as a relatively high density part on a background at a relatively low density.

On the other hand, when a vein is to be imaged, the personal computer 20 generates an image signal component Sp bearing thereon a relatively high density (low brightness) when the level of the off-centered beat signal Bo is lower than the threshold level and otherwise an image signal component Sp bearing thereon a relatively low density (high brightness), and inputs the image signal component Sp into the monitor 21.

The image monitor 21 reproduces a two-dimensional image on the basis of an image signal made up of the image signal components Sp thus generated for the respective scanning spots. In the image, the vein part is shown as a relatively high density part on a background at a relatively low density.

Figure 2:
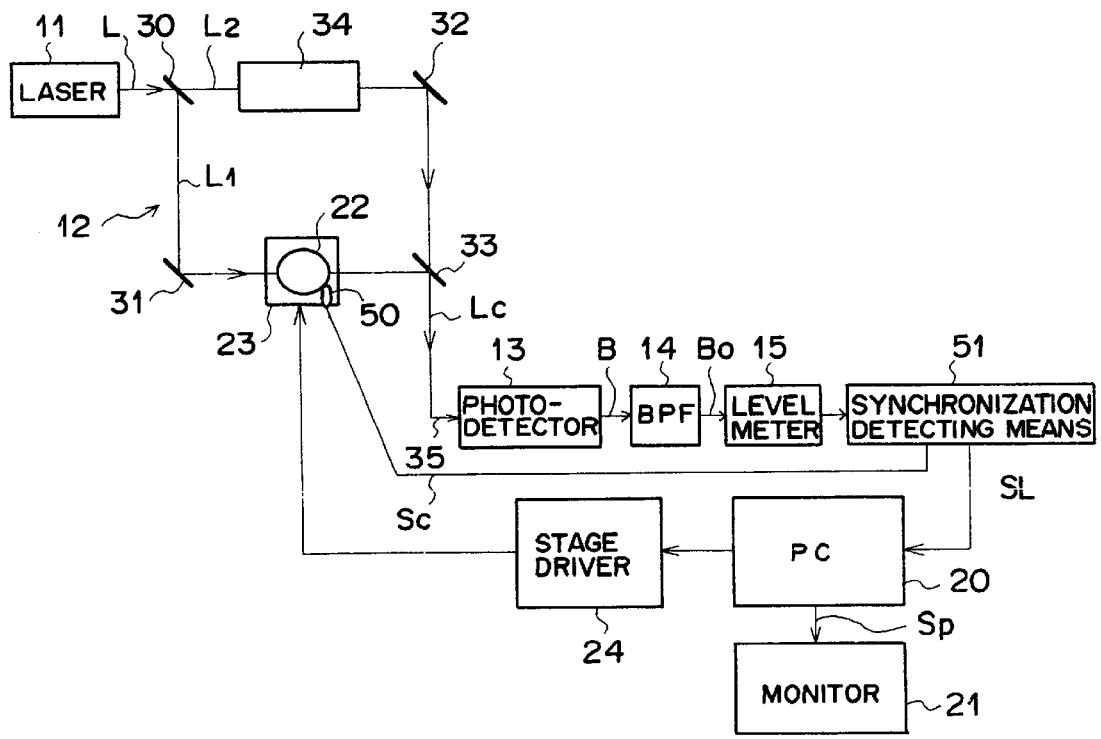
FIG. 2 is a schematic view showing a blood vessel imaging system in accordance with a second embodiment f the present invention.

A blood vessel imaging system in accordance with a second embodiment of the present invention will be described with reference to FIG. 2, hereinbelow. In FIG. 2, the elements analogous to those shown in FIG. 1 are given the same reference numerals and will not be described here. The blood vessel imaging system of this embodiment basically differs from that of the first embodiment in that there are provided a pulsation signal detecting means 50 which detects a pulsation wave of the object 22, and a synchronization detecting means 51 which samples the level signal SL on the basis of a pulsation signal Sc output from the pulsation signal detecting means 50.

Figure 6:
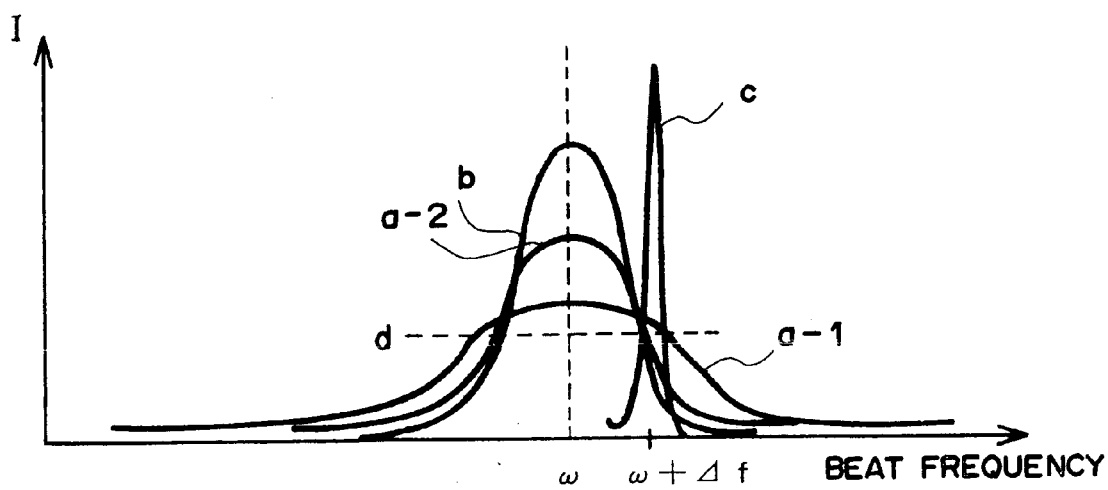
FIG. 6 is a view showing the broadening of the spectrum of the beat signal at different flow rates of hood and the transmission characteristics of the band-pass filter for detecting the off-centered beat signal.

The synchronization detecting means 51 samples the level signal SL at times at which broadening of the spectrum of the beat signal B becomes of a predetermined phase (in this particular embodiment, times at which the flow rate arterial blood is maximized), and inputs the sampled level signal SL into the persona computer 20. With this arrangement, the level of the off-centered beat signal Bo can be detected when broadening of the spectrum of the beat signal B is in a state shown by line a-1 in FIG. 6 far from a state shown by line b representing broadening of the spectrum of the beat signal B when the measuring light beam L travels through a vein, whereby the artery part and the vein part can be imaged clearly distinguished from each other.

Figure 3:
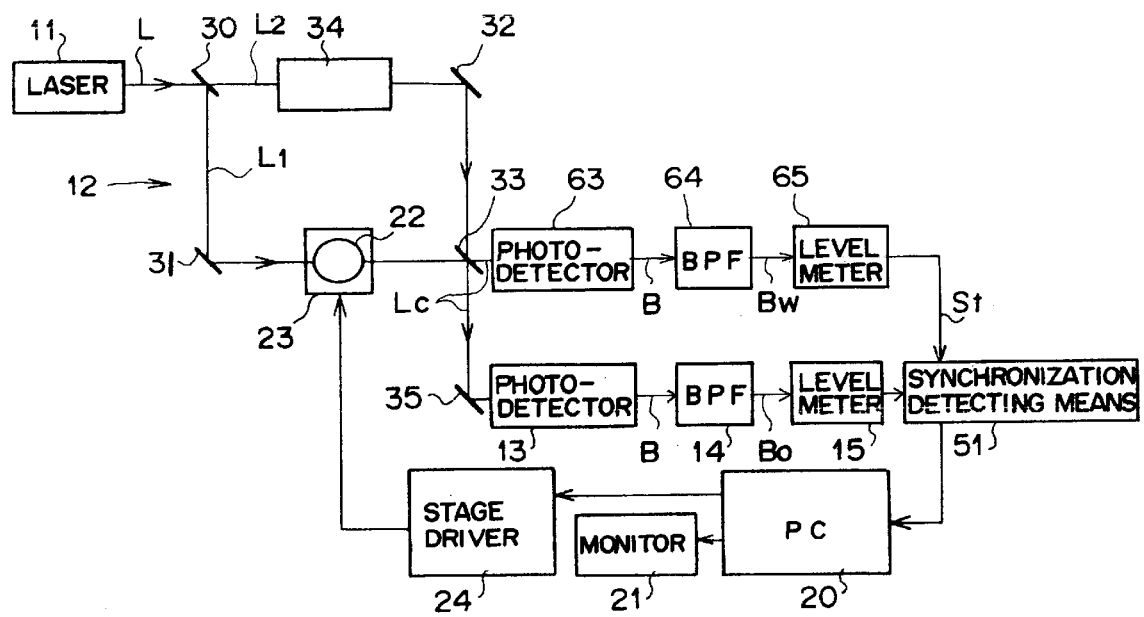
FIG. 3 is a schematic view showing a blood vessel , imaging system in accordance with a third embodiment of the present invention.
Figure 4A:
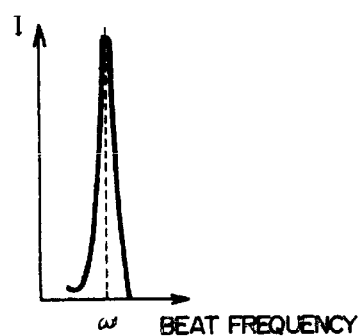
FIGS. 4A to 4D are views for illustrating the relation of the Doppler broadening with the flow rate of fluid.
Figure 4B:
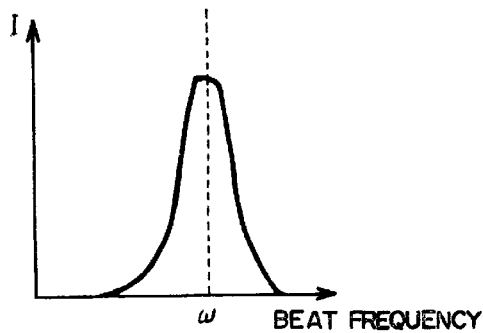
Figure 4C:
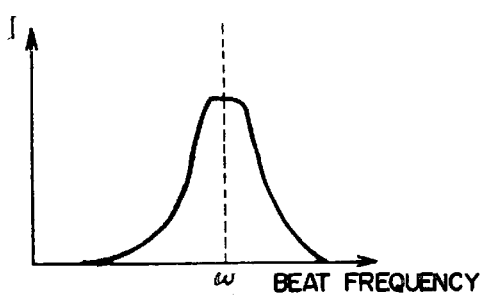
Figure 4D:
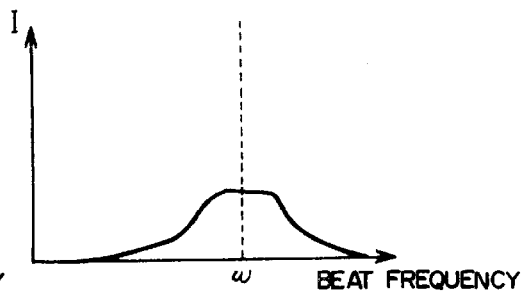

A blood vessel imaging system in accordance with a third embodiment of the present invention will be described with reference to FIG. 3, hereinbelow. In FIG. 3, the elements analogous to those shown in FIG. 2 are given the same reference numerals and will not be described here. The blood ; imaging system of this embodiment basically differs from of the second embodiment in that there are provided, in place of the pulsation signal detecting means 50, a second photodetector 63 which receives the combined light beam Lc, a second band-pass filter 64 which is connected to the photodetector 63 and transmits only a signal in a determined frequency band to be described later, and a second meter 65 which is connected to the band-pass filter 64.

The second band-pass filter 64 selectively transmits signal components in a frequency band near the center frequency $\omega$ of the beat signal B included in the output of the second photodetector 63. The signal B$\omega$ passing through the second band-pass filter 64 is input into the second level meter 65. The second level meter 65 outputs a timing signal St when the peak level of the signal B$\omega$ falls below a preset value and inputs it into the synchronization detecting means 51. The synchronization detecting means 51 samples the level signal SL upon receipt of the timing signal St, and inputs the sampled level signal SL into the personal computer 20.

Also, in this manner, the synchronization detecting means 51 can sample the level signal SL at times at which broadening of the spectrum of the beat signal B becomes of a predetermined phase (in this particular embodiment, times at which the flow rate of the arterial blood is maximized). Accordingly, the level of the off-centered beat signal Bo can be detected when broadening of the spectrum of the beat signal B is in a state shown by line a-1 in FIG. 6 far from a state shown by line b representing broadening of the spectrum of the beat signal B when the measuring light beam L travels through a vein, whereby the artery part and the vein part can be imaged clearly distinguished from each other.

A blood vessel imaging system in accordance with a fourth embodiment of the present invention will be described with reference to FIG. 7, hereinbelow. In FIG. 7, a blood vessel imaging system in accordance with this embodiment comprises a laser 111 emitting a measuring light beam L at a wavelength of $\lambda$, an optical heterodyne optical system 112, first to third photodetectors 113 to 115 which receive the measuring light beam L emanating from the optical heterodyne optical system 112, first to third band-pass filters (BPF) 116 to 118 which are respectively connected to the photodetectors 113 to 115 and selectively transmit signals in predetermined frequency bands to be described later, and first to third level meters 119 to 121 respectively connected to the band-pass filters 116 to 118.

The imaging system further comprises a personal computer (PC) 222 which receives outputs of the level meters 119 to 121 and forms an image signal generating means together with the level meters 119 to 121, and an image monitor 123 such as a CRT display connected to the personal computer 122.

Further, there is provided a X-Y stage 125 which is movable in X and Y directions supporting thereon an object (erg., a human finger) 124. A stage driver 126 drives the X-Y stage 125 under the control of the personal computer 122.

The optical system 112 and the photodetectors 113 to 115 form an optical heterodyne detection system. The optic system 112 comprises a first half-silvered mirror 130 which splits the measuring light beam L into a first light beam L1 (the part of the measuring light beam L reflected by the first half-silvered mirror 130) and a second light beam L2 (the part of the measuring light beam L passing through the first half-silvered mirror 130), a first mirror 131 which reflects the first light beam L1 to impinge upon the object 124, a second mirror 132 which reflects the second light beam L2, and a second half-silvered mirror 133 which combines the first light beam L1 passing through the object 124 with the second light beam L2 reflected from the second mirror 132 into a combined light beam Lc and causes the combined light beam Lc to partly impinge upon the first photodetector 113 and partly impinge upon a third half-silvered mirror 135. The optical system 112 further comprises the third half-silvered mirror 135 and a third mirror 136 which reflects the part of the combined light beam Lc passing through the third half-silvered mirror 135 to impinge upon the third photodetector 115. The third half-silvered mirror 135 reflects a part of the combined light beam Lc to impinge upon the second photodetector 114 and transmits the other part of the combined light beam Lc.

A frequency shifter 134 provided on the optical path of the second light beam L2 shifts the second light be s by a predetermined amount so that the center frequency of the light beam L2 becomes $\omega$. The frequency shifter 134 may comprise, for instance, an AOM.

Operation of the blood vessel imaging system of this embodiment will be described, hereinbelow. When taking a blood vessel image, a measuring light beam L is emitted from the laser 111 and the first light beam L1 is projected onto the object 124. While projecting the first light beam L1, the X-Y stage 125 is moved in X and Y directions, whereby the first light beam L1 is caused to two-dimensionally scan the object 124.

When the first light beam L1 passing through the object 124 is combined with the frequency-shifted second light beam L2 by the second half-silvered mirror 133 into a pair of combined light beams Lc, each of the combined light beams Lc includes therein beat components whose center frequency is $\omega$, equal to that of the frequency-shifted second light beam L2. The outputs of the photodetectors 113 to 115 upon receipt of the combined light beam Lc include a beat signal B generated by the beat components. The outputs of the photodetectors 113 to 115 are respectively input into the band-pass filters 116 to 118.

Figure 8:
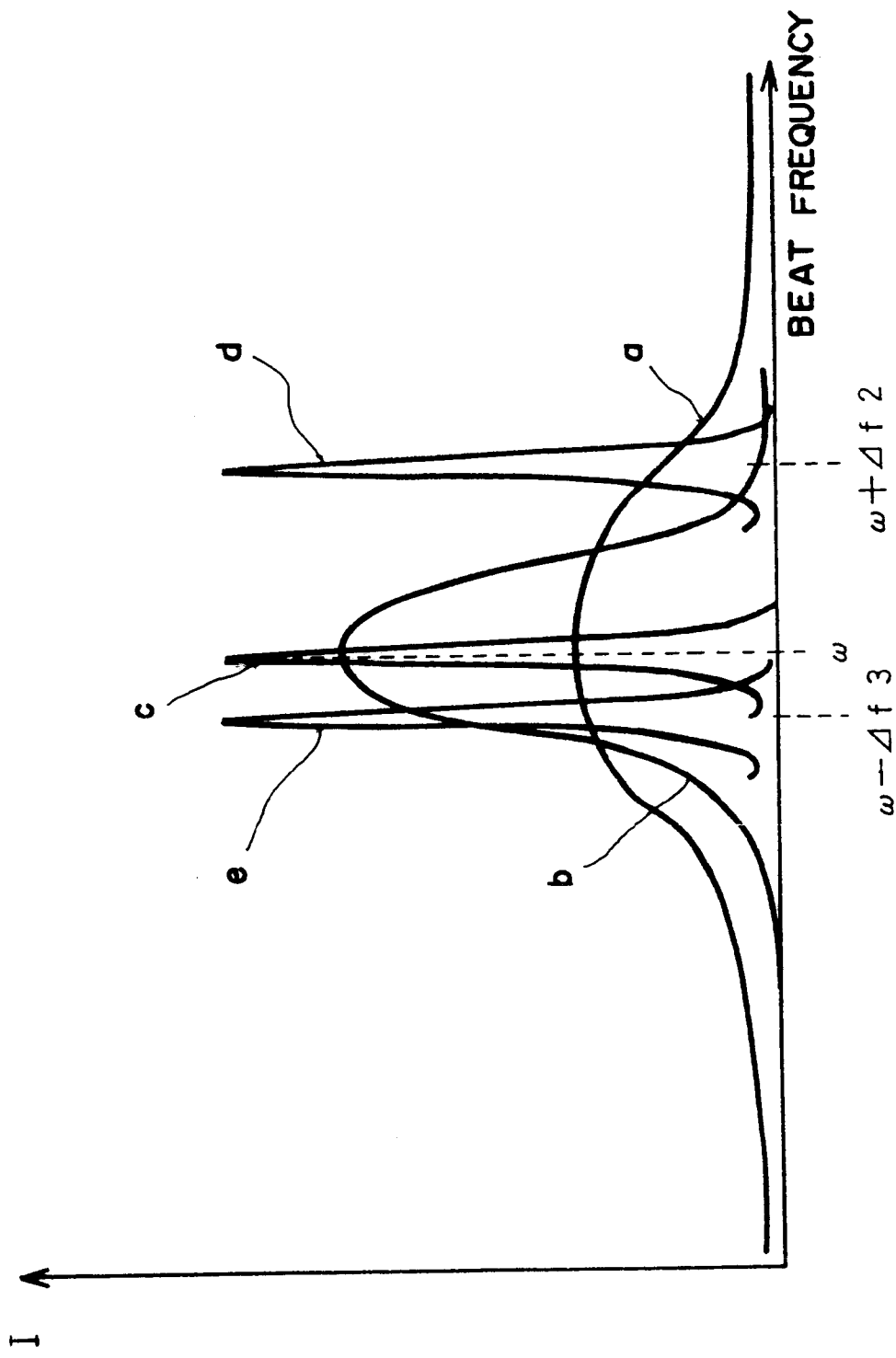
FIG. 8 is a view showing the broadening of the spectrum of the beat signal by flow of blood and the transmission characteristics of the band-pass filters employed in the fourth embodiment to detect the off-centered beat signals.

The spectrum of the beat signal B becomes as shown by line a in FIG. 8 when the first light beam L1 passes through an artery part and as shown by the line b in FIG. 8 when the first light beam L1 passes through a vein part. As described above with reference to FIGS. 11A to 11D, the peak value of the intensity of the beat signal B becomes lower and the spectrum of the beat signal is broadened as the flow rate of the blood increases.

The beat signal B represents intensity of only straight light components traveling straight through the object 124, which is a scattering medium, or scattered light components close to the straight light components. Accordingly, by obtaining an image signal for the object 124 on the basis of the beat signal B, a high spatial resolution can be ensure though the measuring light beam L (the first light beam L1) is scattered by the object 124.

The band-pass filter 116 selectively transmits signal components in a frequency band near the center frequency $\omega$ of the beat signal B as shown by line c in FIG. 8. The band-pass filter 117 selectively transmits signal components in a frequency band near the frequency ($\omega+\Delta f2$) deviated from the center frequency $\omega$ of the beat signal B toward the higher frequency side by a predetermined width $\Delta f2$ as shown by line d in FIG. 8. The band-pass filter 118 selectively transmits signal components in a frequency band near the frequency ($\omega-\Delta f3$) deviated from the center frequency $\omega$ of the beat signal B toward the lower frequency side by a predetermined width Δf3 as shown by line e in FIG. 8. The widths Δf2 and Δf3 are set so that the former is larger than the latter, that is, Δf2 >Δf3.

The outputs of the band-pass filters 116 to 118 are respectively input into the level meters 119 to 121. The level meters 119 to 121 measure levels of the input signals at a predetermined timing, e.g., at a time at which the signal levels are maximized, and input signals representing the measured levels of the signals B(ω), B(ω+Δf2) and B(ω−Δf3) to the personal computer 122.

The personal computer 20 calculates an intensity ratio I((ω+Δf2)/I(ω) when an artery is to be imaged, and generates an image signal component Sp which bears thereon a higher density (lower brightness) as the intensity ratio increase, and inputs the image signal component Sp into the monitor 123. The image monitor 123 reproduces a two-dimensional image on the basis of an image signal made up of the image signal components Sp thus generated for the respective scanning spots. In the image, the artery part is shown as a relatively high density part.

On the other hand, when a vein is to be imaged, the personal computer 20 calculates an intensity ratio I(ω−Δf3)/I(ω), and generates an image signal component Sp which bears thereon a higher density (lower brightness) as the intensity ratio decreases, and inputs the image signal component Sp into the monitor 123. The image monitor 123 reproduces a two-dimensional image on the basis of an image signal made up of the image signal components Sp thus generated for the respective scanning spots. In the image, the vein part is shown as a relatively high density part.

It is possible to show only an artery part or a vein part as a two-valued image by processing the value of the intensity ratio I(ω+Δf2)/I(ω) or I(ω−Δf3)/I(ω) with a threshold value. However, when the image signal component Sp is generated in the manner described above, also the flow rate distribution in the blood vessel can be displayed as difference in image density, which is more advantageous in diagnosis.

Further it is possible to switch between display of an artery image and that of a vein image on the basis of only one of the intensity ratios I(ω+Δf2)/I(ω) and I(ω−Δf3)/I(ω). For example, the image signal component Sp is generated so that the image signal components bears thereon a higher density as the intensity ratio I (ω+Δf2)/I(ω) increases when an artery image is to be displayed, and the image signal components bears thereon a higher density as the intensity ratio I(ω+Δf2)/I(ω) decreases when a vein image is to be displayed.

However when the image signal component Sp is generated in the manner described above, it becomes unnecessary to generate an image signal component Sp representing a vein image on the basis of an extremely small value (close to 0) of the intensity ratio I(ω+Δf2)/I(ω) or to generate an image signal component Sp representing an artery image on the basis of an extremely large value (close to 1) of the intensity ratio I(ω−Δf3)/I(ω), whereby handling of the signals is facilitated.

Figure 9:
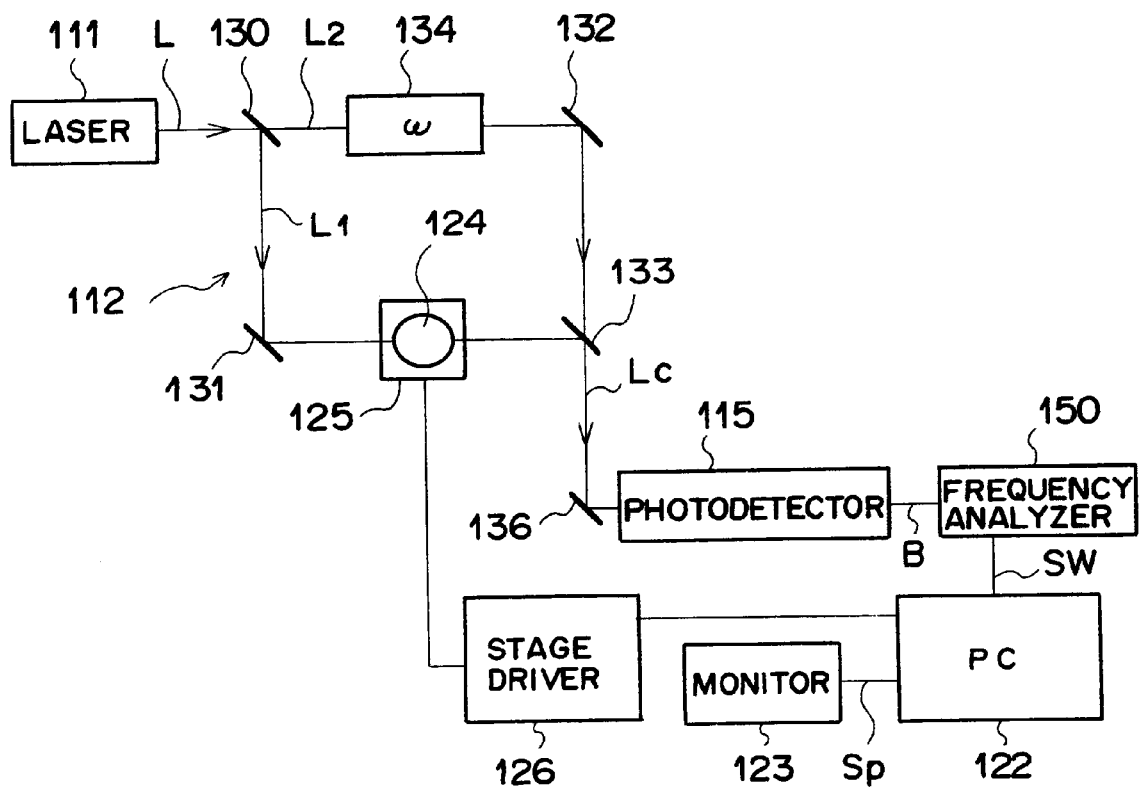
FIG. 9 is a schematic view showing a blood vessel imaging system in accordance with a fifth embodiment of the present invention.

A blood vessel imaging system in accordance with a fifth embodiment of the present invention will be describe with reference to FIG. 9, hereinbelow. In FIG. 9, the elements analogous to those shown in FIG. 7 are given the same reference numerals and will not be described here.

In this embodiment, the frequency-shifted second light beam L2 and the first light beam L1 passing through the object 124 are combined into a single combined light beam Lc by the second half-silvered mirror 133, and the single combined light beam Lc is reflected by a mirror 136 to impinge upon a single photodetector 115. The beat signal B output from photo 115 is input into a frequency analyzer 150 and the output the frequency analyzer 150 is input into the personal computer 122.

Figure 10:
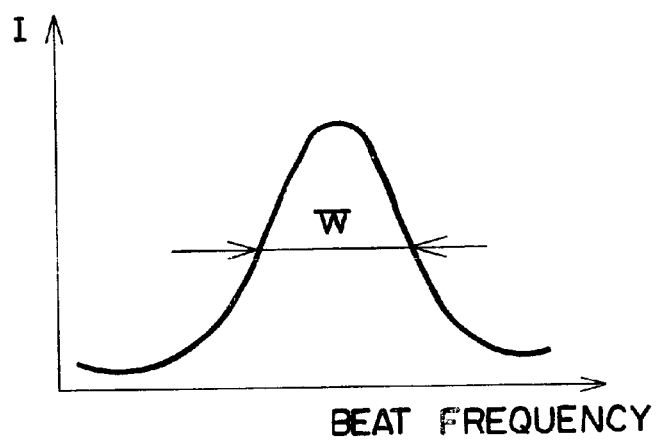
FIG. 10 is a view for illustrating the half-width of the beat signal to be obtained in the fifth embodiment.
Figure 11A:
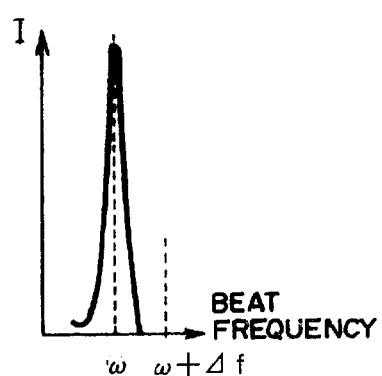
FIGS. 11A to 11D are views for illustrating the relation of the Doppler broadening with the flow rate of fluid.
Figure 11B:
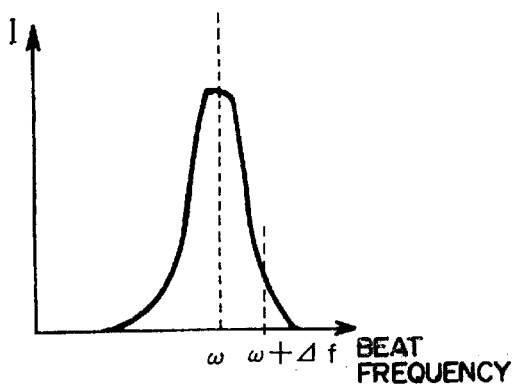
Figure 11C:
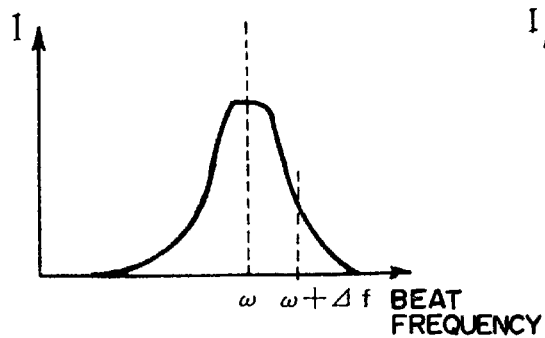
Figure 11D:
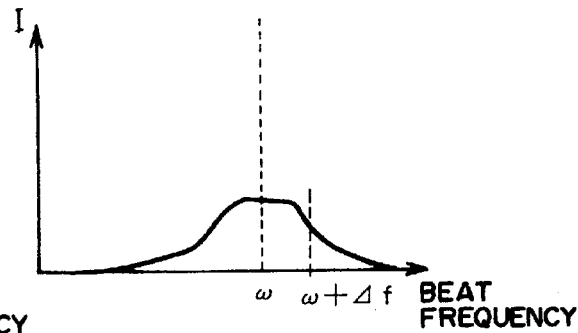
Figure 12:
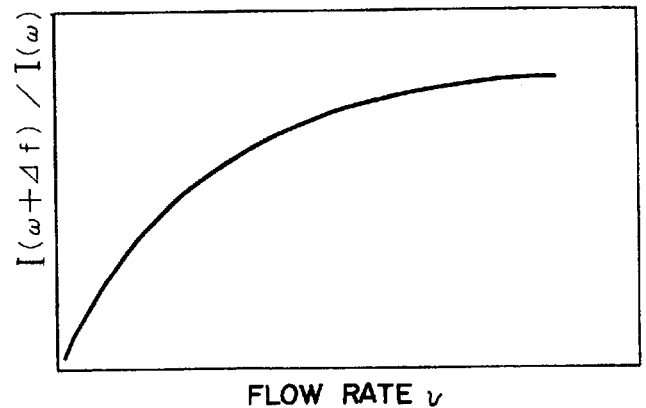
FIG. 12 is a view for illustrating the relation between the intensity ratio $I(\omega+\Delta f)/I(\omega)$ and the flow rate.

The frequency analyzer 150 obtains the spectrum of the beat signal B, and obtains a half width W (full width at half maximum) of the spectrum. As shown in FIG. 10, the half width W is a spectral width between two frequencies at which the intensity of the beat signal B becomes a half of the intensity of the beat signal B at the center frequency ω, at which the intensity of the beat signal B is maximized. Then the frequency analyzer 150 inputs a signal SW representing the half width W into the personal computer 122.

The personal computer 122 generates an image signal component Sp which bears thereon a higher density (lower brightness) as the half width W increases, and inputs the image signal component Sp into the monitor 123. The image monitor 123 reproduces a two-dimensional image on the basis of an image signal made up of the image signal components Sp thus generated for the respective scanning spots. In the image, the artery part is shown as a relatively high density part while the vein part is shown as a relatively low density part.

It is possible to show only an artery part or a vein part as a two-valued image by processing the signal SW with a threshold value.

Figure 13:
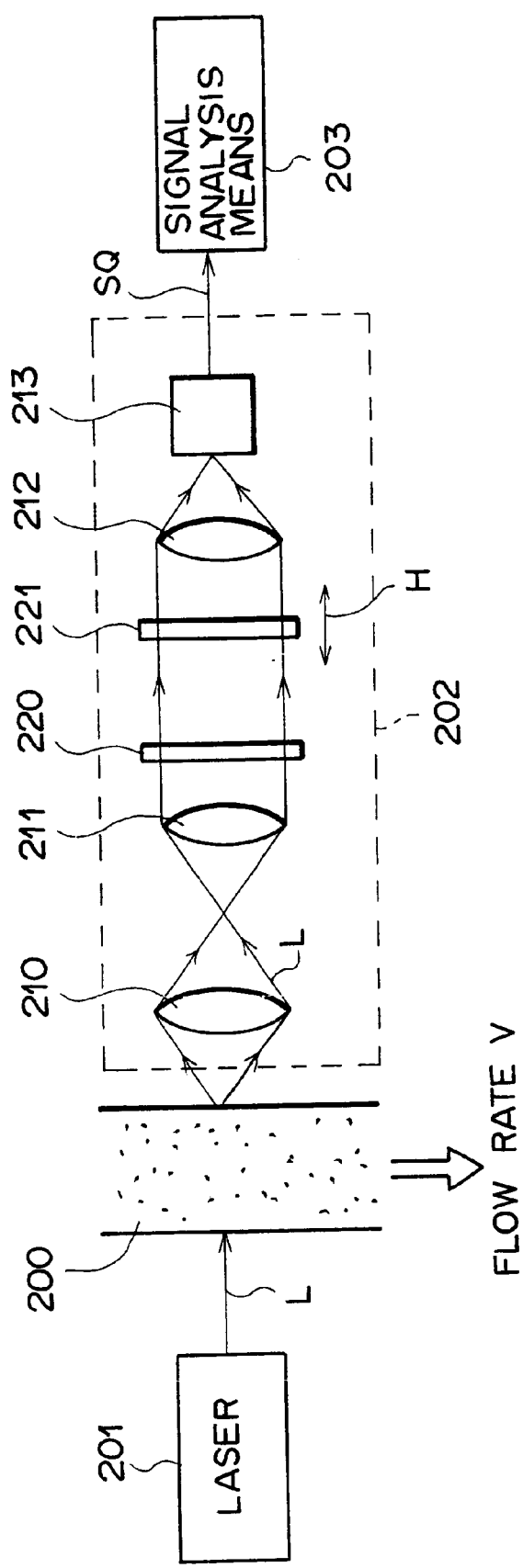
FIG. 13 is a schematic view showing a flow rate measuring system in accordance with a sixth embodiment of the present invention.
Figure 14A:
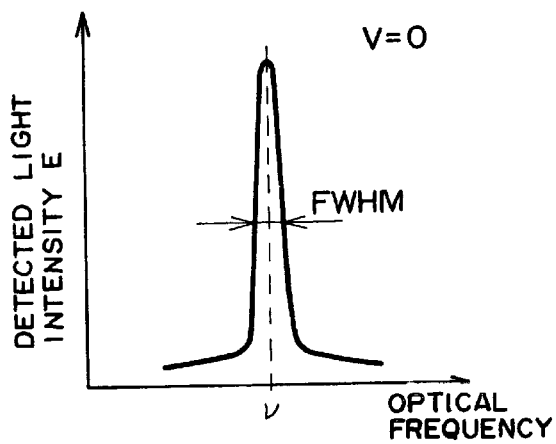
FIGS. 14A to 14D are views showing the change spectrum of the measuring light scattered by the scattering fluid with the flow rate of the fluid.
Figure 14B:
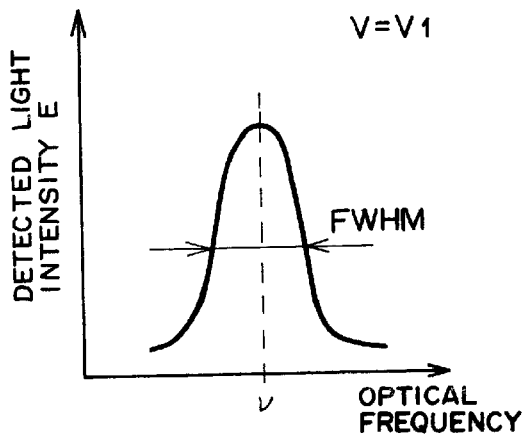
Figure 14C:
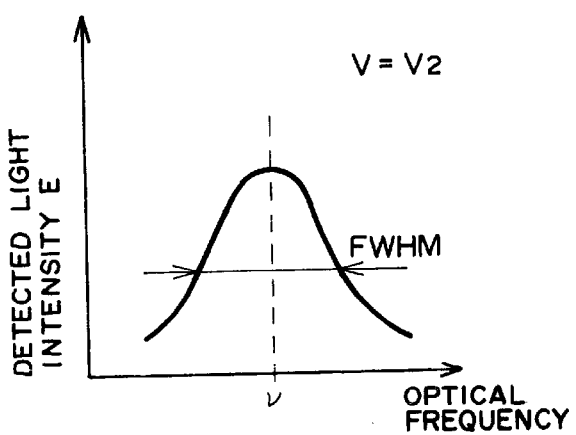
Figure 14D:
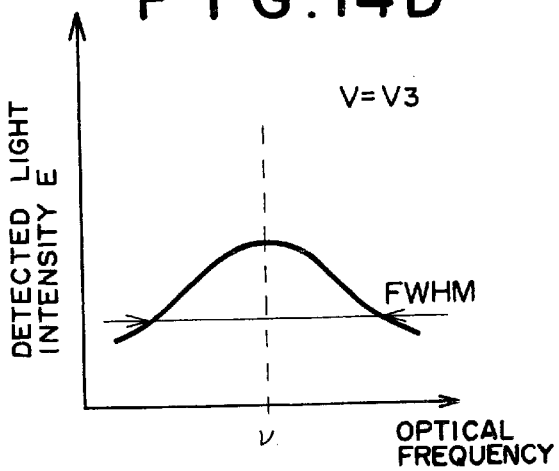

A flow rate measuring system in accordance with a sixth embodiment of the present invention will be described with reference to FIG. 13, hereinbelow.

The flow rate measuring system of this embodiment comprises a laser 201 which projects measuring light L onto light scattering fluid 200 flowing at a flow rate V, a frequency analysis means 202, and a signal analysis means 203 which forms a flow rate analysis means together with the frequency analysis means 202. The frequency analysis means 202 a condenser lens 210 which condenses the measuring light L scattered by the scattering fluid 200, a collimator lens 211 which parallels the scattered measuring light L condensed by the condensor lens 210, a condenser lens 212 which condenses the measuring light L paralleled by the collimator lens 211, a photodetector 213 which detects the measuring light L condensed by the condensor lens 212, and a pair of half-silvered mirrors 220 and 221 which are disposed between the collimator lens 211 and the condensor lens 212 and form a Fabry-Perot interferometer.

The half-silvered mirror 220 is fixed whereas the half-silvered mirror 221 is moved back and forth in the direction of arrow H by a drive means not shown. The signal analysis means 203 comprises a computer system and a light detection signal SQ is input into the signal analysis means 203 from the photodetector 213.

Operation of the flow rate measuring system of this embodiment will be described, hereinbelow. When measuring the flow rate of the light scattering fluid 200, the measuring light L is projected onto the fluid 200. The measuring light L scattered by the fluid 200 is caused to impinge upon the photodetector 213 by the condenser lens 210, the collimator lens 211 and the condenser lens 212 and the amount of measuring light L is detected by the photodetector 213. At this time, light components at wavelengths (frequencies) which generate standing wave between the half-silvered mirrors 221 and 220 enhance each other by light interference, and the light components of the measuring light L at the frequencies are detected by the photodetector 213. When the half-silvered mirror 221 is moved in one direction and the distance of the half-silvered mirror 221 from the half-silvered mirror 220 continuously changes, the frequency of the light components detected by the photodetector 213 continuously changes.

Accordingly, the light detection signal QS output from the photodetector 213 as the half-silvered mirror 221 is moved in one direction represents the intensity E of the detected light component at each frequency. The relation between the frequency and the intensity E of the detected light component varies with the flow rate of the fluid 200 as shown in FIGS. 14A to 14D. FIGS. 14A to 14D respectively show the relations when the flow rate V of the fluid 200 is 0, V1, V2 and V3 (V1<V2<V3). In FIGS. 14A to 14D, v represents-the center frequency.

Figure 15:
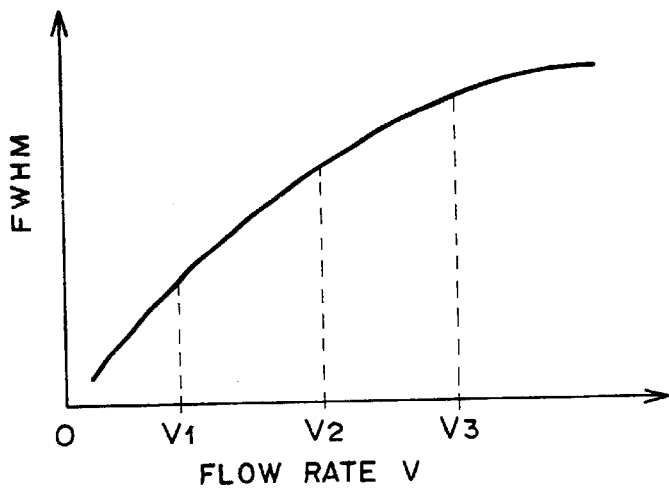
FIG. 15 shows the relation between the half width of the spectrum of the measuring light scattered by the scattering fluid and the flow rate of the fluid.

That is, also in this case, broadening of spectrum detected light due to interaction of the measuring light L with the fluid 200 occurs like the beat signal shown in FIGS. 4A to 4D, and the peak value of the intensity E of detected light becomes lower and broadening of spectrum is enlarged as the flow rate V of the fluid 200 increases as can be seen from FIGS. 14A to 14D. That is, the relation between the half width FWHM and the flow rate V is as shown in FIG. 15. The signal analysis means 203 receives the light detection signal QS and obtains the half width FWHM of the spectrum. Then the signal analysis means 203 determines the flow rate V on the basis of the relation between the half width FWHM and the flow rate V which has been empirically determined. The flow rate V thus determined is shown by a display means such as a liquid crystal panel.

Figure 16:
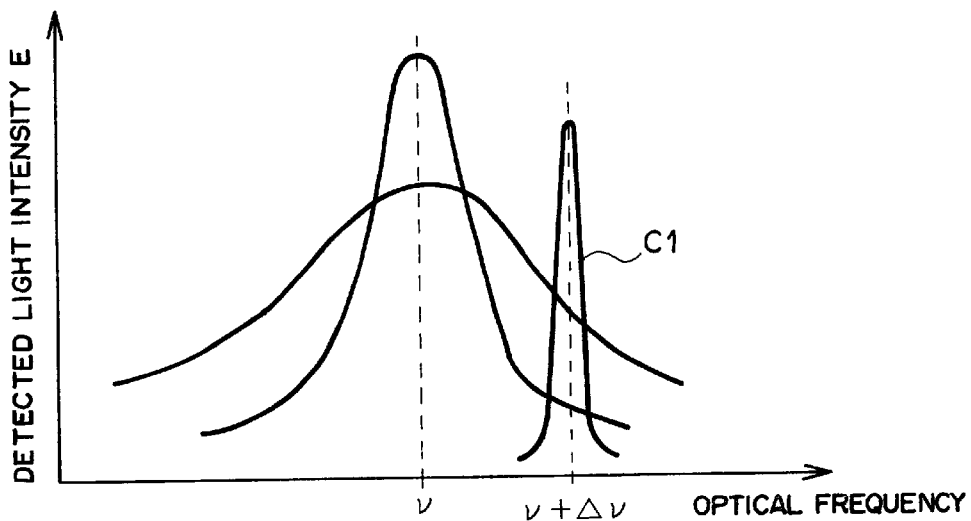
FIG. 16 is a view showing the spectrum of treasuring light scattered by the scattering fluid together transmission characteristic of the filter detecting the off-centered components.

Though, in the embodiment described above, the flow rate V is determined on the basis of the spectrum half width FWHM of the detected light, the flow rate V may be determined on the basis of broadening of detected light spectrum by other methods. For instance, when the light detection signal QS output from the photodetector 213 is passed through a band-pass filter whose stransmission characteristic is such that the center frequency is deviated from the center frequency v of the detected light by $\Delta v$ (off-centered frequency components) as shown by c1 in FIG. 16, the intensity of the frequency components transmitted through the band-pass filter is higher as the broadening of the spectrum increases, i.e., the flow rate V increases. Accordingly, the flow rate V can be obtained according to the intensity of the off-centered frequency components.

Figure 17A:
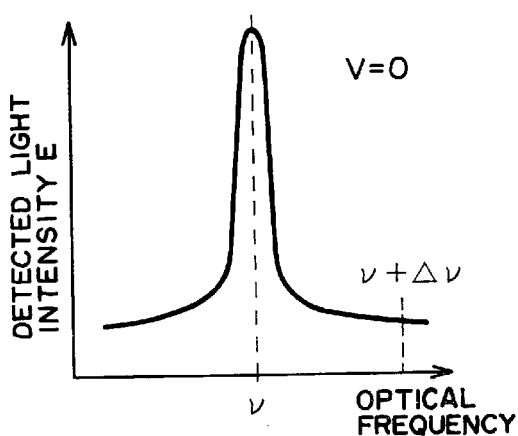
FIGS. 17A to 17C are views showing the change in the spectrum of the measuring light scattered by the scattering fluid with the flow rate of the fluid together with the off-centered frequency.
Figure 17B:
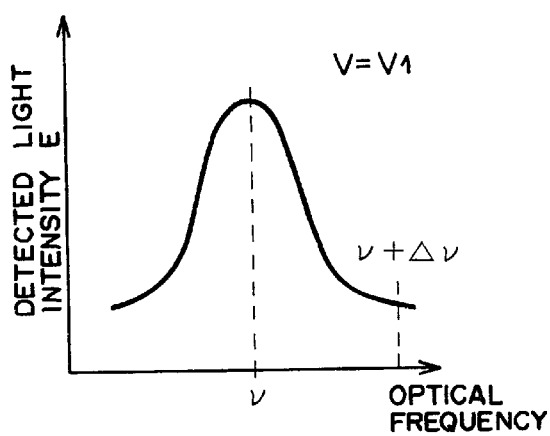
Figure 17C:
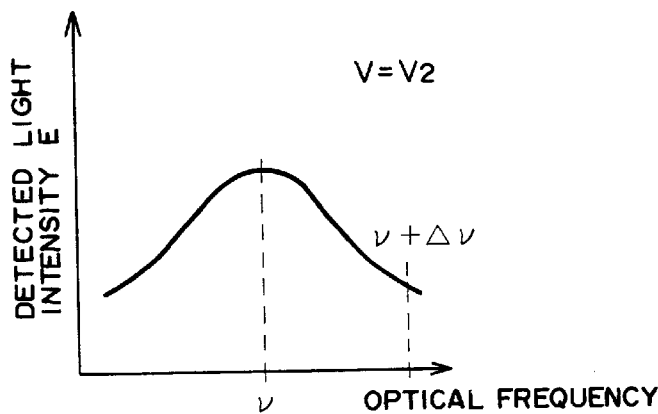
Figure 18:
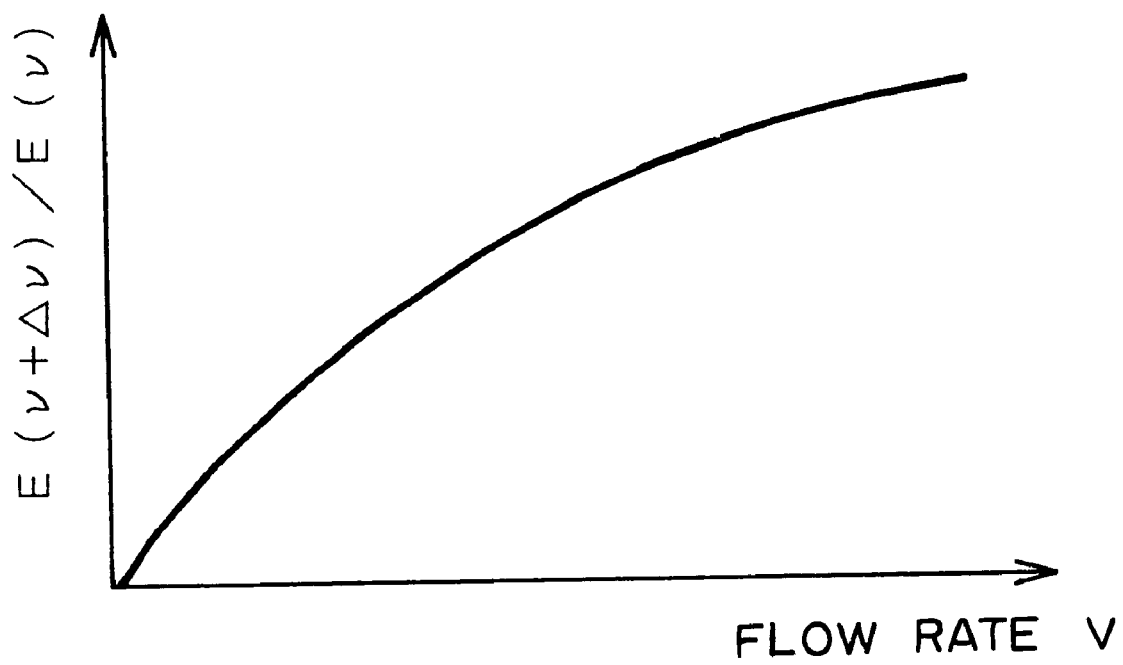
FIG. 18 is a view showing the relation between the ratio between the intensity of the components of the detected light at the center frequency and the intensity of the components at a frequency deviated from the center frequency by a predetermined width and the flow rate of the fluid.

Further when the intensity $E(v)$ of the components of the detected light at the center frequency v and the intensity $E(v+\Delta v)$ of the components of the detected light at the frequency $(v+\Delta v)$ are obtained and the intensity ratio $E(v+\Delta v)/E(v)$ is obtained as shown in FIGS. 17A to 17C, the intensity ratio is higher as the broadening of the spectrum increases, i.e., the flow rate V increases as shown in FIG. 18. Accordingly, the flow rate V can be obtained according to the intensity ratio.

It is possible to measure the flow rate V on the basis of the beat signal detection system output from the optical heterodyne detection system described above. For example, the beat signal B output from the photodetector 115 in the blood vessel imaging system shown in FIG. 9 is larger in reduction of the peak value and in Doppler broadening of the spectrum when the measuring light beam passes through scattering fluid flowing at a higher flow rate as described above with reference to FIGS. 11A to 11D. Accordingly, the half width (FIG. 10) of the spectrum of the beat signal B obtained by the frequency analyzer 150 is larger as the flow rate V of the scatters fluid is larger. Thus, the flow rate V can be determined according to the half width W.

Further when the intensity $I(\omega)$ of the components of beat signal B output from the photodetector 115 at the center frequency $\omega$ and the intensity $I(\omega+\Delta f)$ of the components of the beat signal B at the frequency $(\omega+\Delta f)$ are obtained and the intensity ratio $I(\omega+\Delta f)/I(\omega)$ is obtained, the intensity ratio is higher as the Doppler broadening of the spectrum of the beat signal B increases, i.e., the flow rate V increases.

Accordingly, the flow rate V can be obtained according to the intensity ratio.

Further, the level signal SL output from the synchronization detecting means 51 in the blood vessel imaging system shown in FIG. 3 represents a higher level when the measuring light beam L passes though scattering fluid flowing at a higher flow rate as described above with reference to FIG. 5. Accordingly, the flow rate V can also be obtained according to the level signal SL.

What is claimed is:

1. A blood vessel imaging system comprising
   a measuring light source which emits a measuring light beam,
   a scanning means which causes the measuring light beam to scan an organism,
   an optical heterodyne detection system consisting of an optical system which splits the measuring light beam upstream of the organism into a first light beam traveling to impinge upon the organism and a second light beam traveling not to impinge upon the organism and combines the second light beam with the first beam emanating from the organism into a combined light beam, a frequency shifter which causes the first and second light beams to have frequencies different from each other, and a beat component detecting means which detects beat components of the combined light beam,
   a filtering means which detects, out of the beat component detection signal output from the beat component detecting means, off-centered components in a frequency band deviated from the center frequency of the beat component detection signal by a predetermined width, and
   an image signal generating means which generates an image signal according to whether the off-centered beat signal detected by the filtering means is higher or lower than a predetermined threshold level.

2. A blood vessel imaging system as defined in claim 1 in which the image signal generating means generates an image signal representing artery parts of the organism on the basis of components of the off-centered beat signal which are higher than the predetermined threshold level.

3. A blood vessel imaging system as defined in claim 1 in which the image signal generating means generates an image signal representing vein parts of the organism on the basis of components of the off-centered beat signal which are lower than the predetermined threshold level.

4. A blood vessel imaging system as defined in claim 1 further comprising an in-phase time detecting means which detects in-phase times at which broadening of the spectrum of the beat component detection signal becomes of a predetermined phase, and a synchronization detecting means which samples the off-centered beat signal at the in-phase times and inputs the off-centered beat signal thus obtained into the image signal generating means.

5. A blood vessel imaging system as defined in claim 4 in which the in-phase time detecting means is a means for detecting the pulse wave of the organism.

6. A blood vessel imaging system as defined in claim 4 in which the in-phase time detecting means is a means for detecting the times at which the center frequency component of the beat component detection signal takes a predetermined peak value.

7. A blood vessel imaging system as defined in claim 1 in which the measuring light source comprises a linear or two-dimensional array of a plurality of light emitting portions,
the optical heterodyne detection system is arranged to be able to detect in parallel beat components of the combined light beams based on the measuring light beams from the respective light emitting portions, and
the measuring light source and the optical heterodyne detection system also function as at least a part of said scanning means.

8. A blood vessel imaging system comprising
a measuring light source which emits a measuring light beam,
a scanning means which causes the measuring light beam to scan an organism,
an optical heterodyne detection system consisting of an optical system which splits the measuring light beam upstream of the organism into a first light beam traveling to impinge upon the organism and a second light beam traveling not to impinge upon the organism and combines the second light beam with the first beam emanating from the organism into a combined light beam, a frequency shifter which causes the first and second light beams to have frequencies different from each other, and a beat component detecting means which detects beat components of the combined light beam,
a first intensity detecting means which detects the intensity of center frequency components of the beat component detection signal output from the beat component detecting means,
a second intensity detecting means which detects the intensity of off-centered components of the beat component detection signal in a frequency band deviated from the center frequency of the beat component detection signal by a predetermined width, and
an image signal generating means which generates an image signal on the basis of the ratio of the intensity of the off-centered components of the beat component detection signal to the intensity of the center frequency components of the beat component detection signal.

9. A blood vessel imaging system as defined in claim 8 in which the second intensity detecting means detects the intensities of first and second off-centered components of the beat component detection signal in different frequency bands, and
the image signal generating means generates an image signal representing artery parts of the organism on the basis of the ratio of the intensity of the center frequency components to that of the first off-centered components and generates an image signal representing vein parts of the organism on the basis of the ratio of the intensity of the center frequency components to that of the second off-centered components.

10. A blood vessel imaging system comprising
a measuring light source which emits a measuring light beam,
a scanning means which causes the measuring light beam to scan an organism,
an optical heterodyne detection system consisting of an optical system which splits the measuring light beam upstream of the organism into a first light beam traveling to impinge upon the organism and a second light beam traveling not to impinge upon the organism and combines the second light beam with the first beam emanating from the organism into a combined light beam, a frequency shifter which causes the first and second light beams to have frequencies different from each other, and a beat component detecting means which detects beat components of the combined light beam,
a spectrum analysis means which obtains the spectrum of the beat component detection signal output from the beat component detecting means, and
an image signal generating means which generates an image signal on the basis of a spectral width between two frequencies at which the intensity of the beat component detection signal takes a predetermined value with respect to the intensity of the center frequency components.

11. A blood vessel imaging system as defined in claim 10 in which the image signal generating means uses, as the spectral width, a half-width of the spectrum obtained by the spectrum analysis means.

12. A blood vessel imaging system comprising
a measuring light projecting means which projects measuring light onto an organism, and
an imaging means which images an artery and/or a vein in the organism on the basis of broadening of a spectrum due to an interaction of the measuring light with the organism.

13. A blood vessel imaging system as defined in claim 12 in which the imaging means detects frequency components of the measuring light scattered by the organism, detects the half-width of the spectrum of the frequency detection signal and images an artery and/or a vein in the organism on the basis of the half-width.

14. A blood vessel imaging system as defined in claim 12 in which the imaging means is a means which detects frequency components of the measuring light scattered by the organism, detects the intensity of off-centered components in a frequency band deviated from the center frequency of the frequency detection signal by a predetermined width and images an artery and/or a vein in the organism on the basis of the intensity.

15. A blood vessel imaging system as defined in claim 12 in which the imaging means is a means which detects frequency components of the measuring light scattered by the organs detects the ratio between the intensity of center frequency components of the frequency detection signal and the intensity of off-centered components in a frequency band deviated from the center frequency of the frequency detection signal by a predetermined width and images an artery and/or a vein in the organism on the basis of the intensity ratio.

16. A blood vessel imaging system as defined in claim 12 in which the imaging means is a means which detects frequency components of the measuring light scattered by the organism on the basis of an optical heterodyne detection signal.

17. A blood vessel distinguishing system comprising
a measuring light projecting means which projects measuring light onto an organism, and
a distinguishing means which distinguishes an artery and a vein in the organism from each other on the basis of broadening of a spectrum due to an interaction of the measuring light with the organism.

18. A blood vessel distinguishing system as defined in claim 17 in which the distinguishing means detects frequency components of the measuring light scattered by the organism, detects the half-width of the spectrum of the frequency detection signal and distinguishes an artery and a vein in the organism from each other on the basis of the half-width.

19. A blood vessel distinguishing system as defined in claim 17 in which the distinguishing means is a means which detects frequency components of the measuring light scattered by the organism, detects the intensity of off-centered components in a frequency band deviated from the center frequency of the frequency detection signal by a predetermined width and distinguishes an artery and a vein in the organism from each other on the basis of the intensity.

20. A blood vessel distinguishing system as defined in claim 17 in which the distinguishing means is a means which detects frequency components of the measuring light scattered by the organism, detects the ratio between the intensity of center frequency components of the frequency detection signal and the intensity of off-centered components in a frequency band deviated from the center frequency of the frequency detection signal by a predetermined width and distinguishes an artery and a vein in the organism from each other on the basis of the intensity ratio.

21. A blood vessel distinguishing system as defined in claim 17 in which the distinguishing means is a means which detects frequency components of the measuring light scattered by the organism on the basis of an optical heterodyne detection signal.

22. A flow rate measuring system for measuring a flow rate of light scattering fluid comprising a measuring light projecting means which projects measuring light onto light scattering fluid, and an analysis means which analyzes the flow rate of the light scattering fluid on the basis of broadening of a spectrum due to an interaction of the measuring light with the light scattering fluid.

23. A flow rate measuring system as defined in claim 22 in which the analysis means analyzes frequency components of the measuring light scattered by the organism, detects the half-width of the spectrum of the frequency detection signal and analyzes the flow rate of the light scattering fluid on the basis of the half-width.

24. A flow rate measuring system as defined in claim 22 in which the analysis means is a means which detects frequency components of the measuring light scattered by the organism, detects the intensity of off-centered components in a frequency band deviated from the center frequency of the frequency detection signal by a predetermined width and analyzes the flow rate of the light scattering fluid on the basis of the intensity.

25. A flow rate measuring system as defined in claim 22 in which the analysis means is a means which detects frequency components of the measuring light scattered by the organism, detects the ratio between the intensity of center frequency components of the frequency detection signal and the intensity of off-centered components in a frequency band deviated from the center frequency of the frequency detection signal by a predetermined width and analyzes the flow rate of the light scattering fluid on the basis of the intensity ratio.

26. A flow rate measuring system as defined in claim 22 in which the analysis means is a means which detects frequency components of the measuring light scattered by the organism on the basis of an optical heterodyne detection signal.

\* \* \* \* \*